United States Patent [19]

Maus et al.

[11] 4,274,283
[45] Jun. 23, 1981

[54] APPARATUS AND METHOD FOR MEASURING FLUID GEL STRENGTH

[75] Inventors: L. Donald Maus; George G. Binder, Jr., both of Houston, Tex.

[73] Assignee: Exxon Production Research Company, Houston, Tex.

[21] Appl. No.: 77,219

[22] Filed: Sep. 20, 1979

Related U.S. Application Data

[63] Continuation-in-part of Ser. No. 952,022, Oct. 16, 1978, abandoned, which is a continuation-in-part of Ser. No. 883,555, Mar. 6, 1978, abandoned.

[51] Int. Cl.³ .............................................. E21B 47/06
[52] U.S. Cl. ..................................... 73/153; 73/64.1; 73/438
[58] Field of Search ............... 73/151, 155, 64.1, 61.4, 73/434, 438, 153; 166/250

[56] References Cited

U.S. PATENT DOCUMENTS

| | | | |
|---|---|---|---|
| 2,451,604 | 10/1948 | Barnes | 73/438 |
| 2,607,222 | 8/1952 | Lane | 73/56 |
| 3,839,914 | 10/1974 | Modisette et al. | 73/438 |
| 3,911,740 | 10/1975 | Calhoun | 73/153 |

*Primary Examiner*—Jerry W. Myracle
*Attorney, Agent, or Firm*—Robert B. Martin

[57] ABSTRACT

A method and apparatus for determining the gel strength of drilling mud by the repetitive steps of: flowing mud through a conduit positioned in a nonhorizontal attitude at a flow rate where the shear rate of the mud is in the range of greater than zero to about 20 sec.$^{-1}$, interrupting the flow of mud to provide a static column of mud in the conduit, and measuring the differential pressure of the mud between vertically spaced points during both the flow and static intervals.

22 Claims, 11 Drawing Figures

APPARATUS AND METHOD FOR MEASURING FLUID GEL STRENGTH

CROSS-REFERENCE TO RELATED APPLICATIONS

This application is a Continuation-in-Part of application Ser. No. 952,022, filed Oct. 16, 1978 now abandoned which was a Continuation-in-part of application Ser. No. 883,555, filed Mar. 6, 1978, now abandoned.

BACKGROUND OF THE INVENTION

1. Field of the Invention

The present invention relates to a method and apparatus for measuring properties of fluids, in particular the gel strength and/or density of drilling fluids.

2. Description of the Prior Art

In the drilling of wells by rotary drilling techniques, a drilling fluid, referred to as mud, is circulated from the surface through a drill string and back to the surface. The mud serves several important functions in the drilling operation, two of the most important of which are maintenance of hydrostatic pressure on subsurface formations and the suspension and removal of drill solids from the well. To achieve these functions, the mud must be maintained within a carefully controlled density range and gel strength range. The density and gel strength properties of the mud, therefore, are constantly monitored during the drilling operation.

Over the years several instruments for measuring the mud density and gel strength have evolved. Instruments for measuring density range in complexity from the simple mud balance to the rather sophisticated differential pressure mud weight instrument. One prior differential pressure mud weight instrument is sold by Samega under the trade name of Densimeter DMC and is disclosed on Page 5719 of the *Composite Catalog of Oil Field Equipment and Services,* 33rd Revision (1978-79), published by *World Oil.* Other differential pressure measurement instruments are also disclosed in U.S. Pat. Nos. 2,451,604, 3,175,403, 4,059,744 and Dutch Pat. No. 7,407,114. Differential pressure mud weight instruments generally measure the difference in pressure between two vertically spaced points in mud flowing through a conduit. The pressure differential provides an indication of mud density. Although this type of instrument represents an improvement over the mud balance, it still has certain disadvantages. The instrument does not distinguish between hydrostatic pressure and friction pressure and therefore, measurements under certain conditions will indicate densities substantially different from actual densities. Further, differential pressure mud weight instruments are sensitive to the presence of gas in the mud. It is known that gas entrained in the mud has an effect on mud density. At the surface, the gas-cut or aerated mud density would be less than the mud density in the well under pressure. From an operational standpoint, for mud which is to be pumped into a well, the density of the mud under pressure is more meaningful because it more accurately represents the actual mud density in the well and, hence, the hydrostatic pressure exerted by the mud. The effects of air on mud density may be even more pronounced when certain lost circulation materials such as straw or other fibrous matter are present in the mud because these materials tend to entrain air.

It is also often desired to measure the density of mud as it returns from the well in order to detect the presence of gas or other formation fluids. In this instance, it is generally desirable to measure the density at atmospheric pressure.

Other instruments for measuring mud weight or density are disclosed in U.S. Pat. No. 2,609,681 and Canadian Well Logging Society Paper No. 7065 presented in Calgary, May 6-8, 1970.

Gel strength, defined as the property of a mud to develop and retain rigid form, is an important measure of the mud's ability to suspend drilled solids in a quiescent condition. The gel strength should be sufficiently high to suspend the solids, but not so high as to retard drilling operations. A common instrument for measuring gel strength is the Fann V-G meter. This instrument, however, does not provide a continual record or comparison of the mud gel strength at frequent time intervals. U.S. Pat. No. 3,069,900 discloses apparatus and method for measuring mud properties (viscosities and gel strength) of non-Newtonian liquids. Another type of instrument for measuring gel strength and viscosities is disclosed in British Pat. No. 1,280,227. The gel strength instrument generally comprises a horizontally disposed pipe loop having two pressure taps located along its length. The mud is introduced into the loop and allowed to set for a predetermined time. Flow is then initiated and the peak pressure difference between the two taps is directly proportional to the gel strength.

SUMMARY OF THE INVENTION

The present invention provides method and apparatus for accurately determining properties of drilling mud. Briefly, the method of the present invention involves determining the gel strength of the mud by the repetitive steps of: flowing mud through a conduit positioned in a nonhorizontal attitude at a flow rate where the shear rate of the mud is in the range of greater than zero at about 20 sec.$^{-1}$, interrupting the flow of mud to provide a static column of mud in the conduit, and measuring the differential pressure of the mud between vertically spaced points during both the flow and static intervals. It has been found that the difference between the flow differential pressure and the static differential pressure provides an indication of the gel strength of the mud. The gel strength property of mud is important because of the necessity of the mud to suspend solids in the well under quiescent conditions. By recording both the flowing and static measurements, cycled at frequent intervals, a virtually continuous record of the mud gel strength may be obtained. The continual record permits recognition of changes in this important property of the mud.

A variation in the method for determining gel strength involves reversing the flow through the conduit at frequent time intervals and measuring the differential pressure at vertically spaced points in the conduit in each flow direction, and computing the difference between the two differential pressure measurements. This difference is proportional to the gel strength of the mud.

The apparatus of the present invention measures the gel strength and/or the density of the mud and generally includes a conduit positioned in a nonhorizontal, preferably vertical, attitude; means for determining the pressure differential between vertically spaced locations in the conduit; and means for cycling mud flow through the conduit to create alternating flowing and static columns between the spaced locations. In the embodiment of the apparatus for measuring gel strength, the apparatus includes means for flowing the mud through the conduit at a flow rate where the shear rate of the flowing mud is in the range of greater than zero to about 20 sec$^{-1}$. In one embodiment of the apparatus for measuring the density of the mud to be pumped into the well, the apparatus includes a valve capable of maintaining a desired amount of back pressure on the mud column to compress entrained gas in the mud. Because of the tendency of mud to cake and plug, the back pressure valve should be an elastomeric-sleeve pinch-type valve which throttles flow by deforming inwardly to create the desired back pressure. In another embodiment of the apparatus for measuring the density of mud returning from a well, the apparatus is provided with an outwardly flared inlet disposed in a generally vertical attitude to prevent intake of large drill cuttings into the apparatus.

An advantage of the present invention is that it provides a substantially continuous determination of desired properties of drilling mud. The apparatus is a simple, rugged configuration and readily adapted to field operations. For example, it may be employed to test fluids from a fluid pit or a flowing line. A further feature of the present invention is its ease of calibration. These and other advantages and features will become apparent from the following discussion.

DESCRIPTION OF THE PREFERRED EMBODIMENTS

Figures 2, 3:
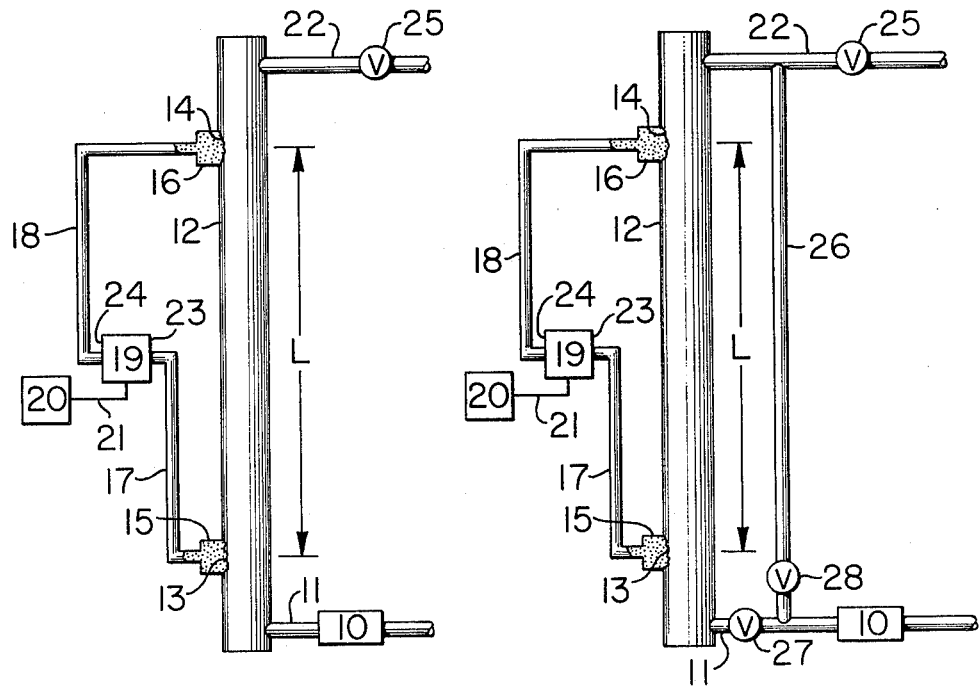
FIG. 2 is a schematic diagram illustrating one embodiment of the apparatus of the present invention.
FIG. 3 is a schematic diagram illustrating another embodiment of the apparatus of the present invention.

The present invention will be described with reference to its application in measuring the properties of a drilling mud. It should be understood, however, that it may be also used in measuring the properties of any viscous, non-Newtonian fluid. With reference to FIG. 2, the apparatus includes a vertical gauge conduit or tube 12 closed at its opposite ends and having an inlet line 11 and discharge line 22. A pump 10 is adapted to pump a mud sample from the mud system through inlet line 11, through gauge conduit 12, out discharge line 22, and back to the mud system. The present invention will be described in terms of upward flow through gauge conduit 12, which is the preferred direction to minimize settling of solid materials from the mud. However, downward flow is also possible. Modifications to the following description to accommodate downward flow will be obvious to one skilled in the art.

The means for measuring the differential pressure at vertically spaced locations within gauge conduit 12 include two flexible isolation diaphragms 13 and 14 vertically spaced apart by distance L. The diaphragms separate the interior of the gauge conduit 12 from chambers 15 and 16, respectively, defined by suitable housings. Chambers 15 and 16 are in fluid communication with opposite sides 23 and 24 of a differential pressure transducer 19 by lines 17 and 18, respectively. The chambers 15 and 16 and the lines leading to the pressure transducer 19 are filled with a noncompressible liquid. In certain applications, it is preferred that a back pressure be maintained on the fluid column by back pressure valve 25. It is preferred that the back pressure valve comprise an elastomeric-sleeve, pinch-type valve such as the Type "DW" valve manufactured by the Red Valve Co.

The system is operated such that the flow of the mud sample through the gauge conduit 12 is intermittent to provide a flow interval and a static interval. In the embodiment illustrated in FIG. 2, the intermittant operation may be achieved by intermittantly operating pump 10 or by intermittantly closing valve 25.

The measurement of differential pressure between diaphragms 13 and 14 during the static interval of the cycle provides an indication of mud density independent of friction.

The pressures in vertical gauge conduit 12 at isolation diaphragms 13 and 14 are transmitted via the noncompressible fluid in chambers 15 and 16 and lines 17 and 18, respectively, to the differential pressure transducer 19, such as the ITT Barton Model 752 Differential Pressure Unit, which senses the pressure difference between isolation diaphragms 13 and 14 and transmits the information as an electrical, mechanical, hydraulic, or pneumatic signal via line 21 to a read-out device 20 such as a gauge and/or recorder which may be calibrated in convenient units (e.g., pounds per gallon).

Another embodiment of the invention is illustrated in FIG. 3 where like reference numerals indicate corresponding components of FIG. 2. The primary difference between the apparatus of FIG. 3 and that of FIG. 2 is in the means for cycling flow through conduit 10. In this embodiment, a bypass line 26 running parallel to gauge conduit 12 interconnects lines 11 and 22. Two valves, 27 and 28, are provided in lines 11 and 26, respectively. Valves 27 and 28 are also preferably elastomeric-sleeve, pinch-type valves, such as the Mini-Flex Series 2600 valves manufactured by the Red Valve Co.

In operation of the apparatus disclosed in FIG. 3, pump 10 is run continuously and, if back pressure is desired, valve 25 maintains a substantially constant back pressure on the gauge conduit 12 and line 26. The valves 27 and 28 are sequentially operated between a first condition in which mud flow is directed through gauge conduit 12 and out line 22 (valve 27 open and 28 closed), and a second condition in which mud is directed through bypass line 26 (valve 27 closed and 28 open). The mud cycling through the gauge conduit 12 produces a flow interval and a static interval in gauge conduit 12.

In both the embodiments disclosed in FIGS. 2 and 3, the mud flow is cycled at a predetermined frequency to provide the alternating static and flowing conditions within gauge conduit 12. The frequency should be sufficiently slow to provide a stabilized reading in each period, but not so slow as to cause the mud to gel excessively during the static condition. Frequencies between about 0.1 and 15 cycles per minute should be satisfactory for most types of mud.

When fluid in the vertical gauge conduit 12 between the two isolation diaphragms 13 and 14 is static, the pressure at diaphragm 13 will be greater than that at diaphragm 14 because of the hydrostatic pressure gradient of the fluid. Read-out device 20 will provide an indication of the true density of the fluid. When mud in the vertical gauge conduit 12 is flowing, read-out device 20 will provide an indication different from the true density due to the frictional pressure gradient of the flowing fluid. It has been found that at low flow rates the difference between static and flowing measurements is proportional to the gel strength. Cycling the flowing and static phases every 20 seconds, for example, produces an accurate and substantially continuous plot of both the gel strength and density of the fluid being sampled similar to those shown in FIGS. 5 and 6.

The principle of operation of the present invention is described below. Under static conditions in the apparatus in FIG. 2, and assuming no pressure loss across the isolation diaphragms 13 and 14, the differential pressure, $\Delta P$, across a transducer 19 may be represented by the equation:

$$\Delta P = (\rho - \rho_f) g L \cos \theta \qquad (1)$$

where
$\rho$ = the density of the fluid in gauge conduit 12
$\rho_f$ = the density of the noncompressible fluid in lines 17 and 18 connecting the isolation diaphragms 13 and 14 to the differential pressure transducer 19,
g = the gravitational constant,
L = the distance between the centers of the isolation diaphragms 13 and 14,
$\theta$ = the angle between the axis of the gauge conduit 12 containing the isolation diaphragms 13 and 14 and vertical.

Hence, in the vertical configuration of the apparatus shown in FIG. 2, $\cos \theta = 1$ and $$\Delta P = (\rho - \rho_f) g L. \qquad (2)$$

Since $\rho_f$, g and L are constant for any given apparatus, the output of the differential transducer can be calibrated to read $\rho$, the fluid density, directly according to $$\rho = (\Delta P / g L) + \rho_f \qquad (3)$$

For upward flowing conditions through gauge conduit 12, the frictional pressure gradient results in apparent fluid densities greater than the actual density as measured in the static environment. The difference in measured fluid density for fluid flowing vertically upward in a pipe can be shown to be:

$$\Delta \rho = 4\tau / g D \qquad (4)$$

where
$\Delta \rho$ = difference in fluid density measurement,
D = inside diameter of gauge conduit 12,
$\tau$ = shear stress at wall of gauge conduit 12.

Figure 1:
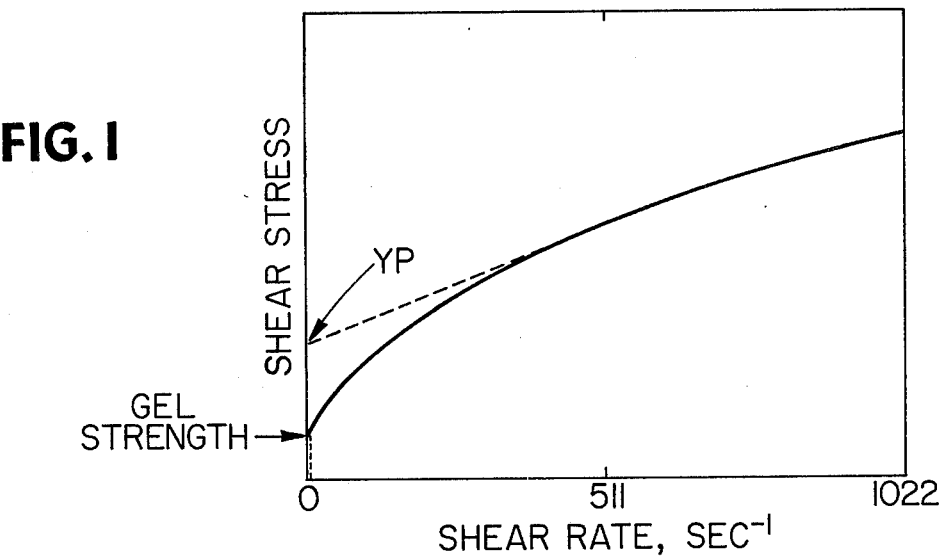
FIG. 1 is a curve representing the rheological behavior of a typical drilling fluid.

The shear stress verses shear rate behavior of a typical water-base clay drilling mud is shown in FIG. 1. This behavior can be considered as having two regions of characteristic behavior depending on the shear rate. Below a shear rate of about 500 sec$^{-1}$, the behavior is often nonlinear, tending toward a non-zero value of shear stress with decreasing shear rate. This value is called the initial gel strength G of the mud. Above 500 sec$^{-1}$, the behavior is generally linear.

Low shear rate behavior is important since this characteristic governs the ability of the mud to suspend weighting materials and to transport drill cuttings from the well. It is known in the art that the gel strength G is a governing property with regard to low shear rate behavior. Because it is somewhat difficult to measure, it is common practice in the drilling industry to determine a related parameter called yield point. This is determined by measuring the shear stress at 511 and 1022 sec$^{-1}$ using a Fann V-G Meter and constructing a straight line through these points. As shown in FIG. 1, the intercept of this line with the shear stress axis is called the yield point, YP. It is known in the art that yield point and gel strength are related and that this fictitious parameter (yield point) can be used to indicate changes in gel strength. However, it does not represent a real property of the mud.

In the past, when gel strength was measured, it was common to measure it immediately upon the initiation of flow after the mud had remained quiescent for a predetermined period of time. The flow rate was low so that there was a corresponding low value of shear rate, typically 5.11 sec$^{-1}$. Such measurement included an error factor attributable to the force required initiate movement of the mud. In the present apparatus, the gel strength is measured during flow rather than upon the initiation of flow. The flow rates are low so that the shear rate in conduit 12 will be low. As a consequence, the shear stress $\tau$ will approximate the gel strength G. Therefore, the gel strength is related to the difference in measured density during flowing conditions by $$G = (gD/4)\Delta \rho \qquad (5)$$

By alternately measuring the density of the mud during flowing and static conditions, the density difference $\Delta \rho$ can be determined and related to the gel strength through Eq. 5.

If it is assumed that flow in the vertical conduit is laminar and the fluid is Newtonian, the shear rate $\gamma$ at the wall of the gauge conduit 12 (assuming a cylindrical conduit) will be $$\gamma = (32/\pi)(Q/D^3) \qquad (6)$$

where Q is the volumetric flow rate in the gauge conduit 12. Although drilling fluids are not generally Newtonian, Eq. 6 is still a reasonable approximation for the wall shear rate. As mentioned previously, in the drilling industry a shear rate of 5.11 sec$^{-1}$ is typically used to measure gel strength. An approximation of this shear rate will be obtained in the present apparatus by circulating at a rate given by $$Q = 0.5 D^3 \text{ (volume/sec)} \qquad (7)$$

which is obtained by substituting 5.11 sec$^{-1}$ for $\gamma$ in Eq. 6 and solving for Q. Using units common in the drilling industry, it is found that the flow rate corresponding to a 5.11 sec$^{-1}$ shear rate in a 4-inch diameter pipe is 8.3 gallons/minute.

Generally, flow rates for operation of the present apparatus and method are preferably adjusted for a shear rate, $\gamma$, at the wall of the gauge conduit in the range of from greater than zero to 20 sec$^{-1}$ using Eq. 6. At these shear rates, the shear stress will adequately approximate the gel strength. As used herein, the terms shear rate and shear stress are understood to be at the wall of the gauge conduit 12.

Thus, in operation, a gauge which has been calibrated to report the fluid density reports the true density when the flow is stopped and reports the true density plus the difference, $\Delta\rho$, when the fluid is moving upward past the isolation diaphragms. Since the density difference is proportional to the gel strength, information on this property is available from the apparatus.

A convenient manner of reporting the density and gel strength of the fluid is to record the output signal from the gauge on a continuous chart recorder. If the fluid in the gauge is alternated between flowing and static conditions at a relatively rapid rate (for example, 10 seconds flowing, 10 seconds static) and the chart is moved relatively slowly (for example, one inch per hour), the movement of the recording pen will create a band (illustrated in FIGS. 5 and 6), the lower edge of which is indicative of the true density and the width of which is proportional (according to Eq. 5) to the gel strength.

Figure 4:
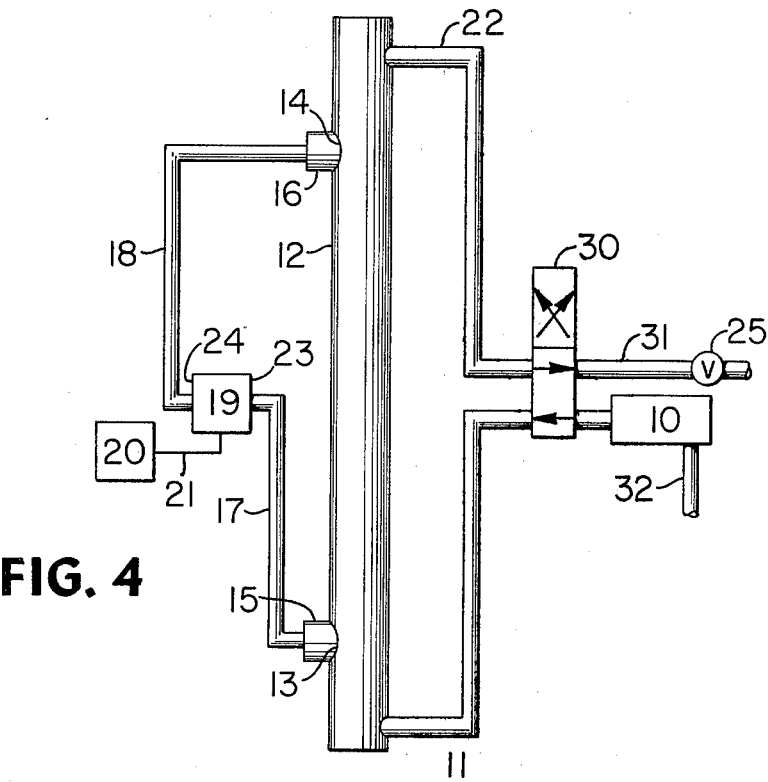
FIG. 4 is a schematic diagram illustrating still another embodiment of the present invention.

FIG. 4 illustrates another embodiment of the invention. The apparatus disclosed in this figure also includes a conduit and differential pressure measuring means which are represented by like reference numerals as in FIGS. 2 and 3. In this embodiment, however, the fluid flow is reversed through the gauge conduit 12.

Pump 10 is capable of continuously pumping fluid to a 4-way, 2-position valve 30. The valve 30 alternately sends the fluid through lines 11 and 22 into the top or bottom of vertical gauge conduit 12. The fluid alternately exits conduits 22 and 11 and passes through valve 30 into conduit 31 which is provided with back pressure valve 25. The means for measuring and displaying or recording differential pressures between vertically spaced locations in gauge conduit 12 may be the same as described in the previous embodiments.

By reversing flow through the vertical gauge conduit 12 and by measuring the pressure differential between two vertically spaced points in the conduit, an accurate and substantially continuous report on the gel strength and density of the fluid being sampled can be determined. When fluid enters the top of gauge conduit 12 through line 22, the readout device 20 will provide an indication of a fluid density that is less than the true density by the amount $\Delta\rho$. When fluid flow is reversed and fluid enters the bottom of gauge conduit 12 through line 11, the readout device 20 will provide an indication of a fluid density that is greater than the true density by the amount $\Delta\rho$.

Figure 7:
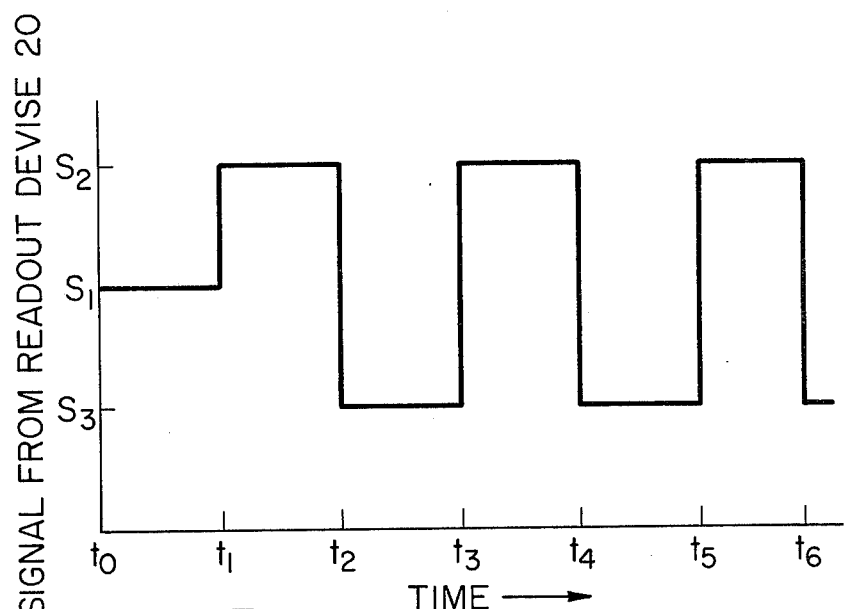
FIG. 7 is an idealized plot illustrating the performance curve of apparatus shown in FIG. 4.

FIG. 7 shows a schematic plot of the signal emitted by readout device 20 as fluid is alternatively flowed upward and downward in gauge conduit 12. During the time period between $t_0$ and $t_1$, pump 10 is shut off and the fluid in gauge conduit 12 is static. At time $t_1$, pump 10 is started and fluid is pumped through line 11. At time $t_2$, valve 30 is shifted to cause the fluid to flow through line 22 into the top of gauge conduit 12. Similarly, at times $t_3$ and $t_4$, the valve 30 is adjusted to cause upward flow in the gauge conduit 12 and at times $t_4$ and $t_6$, valve 30 is shifted to cause downward flow in the gauge conduit 12. Between time $t_0$ and $t_1$, readout device emits a signal $S_1$. From time $t_1$ to $t_2$, fluid flows upward through gauge conduit 12 and read-out device 20 emits a signal $S_2$. From time $t_2$ to $t_3$, fluid flows downward through gauge conduit 12 and readout device 20 emits a signal $S_3$. The average value of signals $S_2$ and $S_3$ is indicative of the true density of the fluid. The difference between signals $S_2$ and $S_3$, $\Delta\rho'$, is twice the value of $\Delta\rho$ obtained from the embodiments of FIGS. 2 and 3. It is proportional to the gel strength G according to $$G=(gD/2)\Delta\rho' \tag{8}$$

A particular advantage of the present apparatus is its ease of calibration, which is particularly desirable for field use where access to fluids of accurately known and varying density is restricted. Calibration requires only that the density, $\rho_f$, of the noncompressible fluid be accurately known. Since this can be determined at the time of manufacture of the apparatus, this value will be considered a known constant.

The ease of field calibration can be seen by considering the differential pressure sensed at the transducer 19 under two specific conditions.

When the apparatus is placed in a horizontal position, $\cos\theta=0$ and Eq. 1 becomes $$\Delta P=0 \tag{9}$$

When the vertical conduit is emptied ($\rho=0$) and turned vertically upside down ($\cos\theta=1$), Eq. 1 becomes $$\Delta P=\rho_f gL \tag{10}$$

Substitution of these $\Delta P$ values into Eq. 2 demonstrates that, when turned horizontal and upside down, the differential pressures sensed by the transducer correspond to those which would be sensed if the apparatus were in its operating position and full of static fluids having densities equal to $\rho_f$ and $2\rho_f$, respectively. This provides two known calibration points without the necessity of filling the apparatus with fluids of known densities. For example, if $\rho_f$ were 9 pounds per gallon which approximates a water-ethylene glycol mixture, the calibration points would be 9 and 18 pounds per gallon. This approximates the normal range of drilling fluids quite well.

FIELD TESTS

The following field tests demonstrate the operability of the present invention and its ability to measure both the true density and gel strength of mud. The tests were performed under actual drilling conditions in which a bentonite water base mud was being circulated in a well. The apparatus used in the tests was similar to FIG. 3, consisting of the following components:

(a) A gauge conduit (12) 72 inches long, 4.0 inches I.D.

(b) Diaphragms (13 and 14) placed 48 inches apart: Differential Pressure Transducer (19): ITT Barton Model 752 Strip Chart Recorder (20) having a variable speed.

Figure 5:
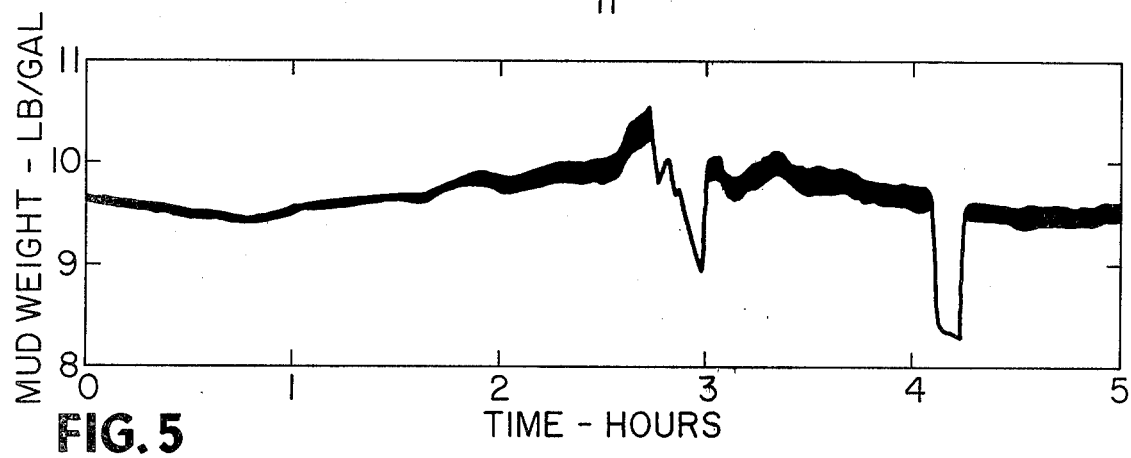
FIGS. 5 and 6 are recordings of mud properties obtained from the apparatus shown in FIG. 3.

(c) A Moyno Model 1L4 progressive cavity pump (d) A ¾-inch back pressure valve (26): Mini-Flex 2600 sold by Red Valve Company The suction line to pump 10 was placed in the tank feeding the mud pumps. The mud was pumped continuously at a rate of 8.7 gallons per minute and the valves 27 and 28 were cycled between the first (through) position and second (bypass) position at 10 seconds to provide a continuous recording as shown in FIG. 5. For the particular apparatus used, Eq. 5 reduced to:

$$G = 47 \Delta \rho \qquad (11)$$

where G has the units of pounds per 100 square feet and $\Delta \rho$ has the units of pounds per gallon. As indicated in FIG. 5, the mud properties during about the first 1.5 hours of testing had a density of about 9.4 to 9.6 pounds per gallon, and the gel strength remained relatively constant at about 3 pounds per 100 square feet. After about 1.5 hours of operations, bentonite was added to increase the gel strength of the mud. As clearly seen in the plot, the thickness of the line increased to a relatively constant value which corresponds to about 9 pounds per 100 square feet. The density also increased which is attributed to the higher viscosity mud picking up barite which had settled in the tanks. At about 2.8 hours, water was added to dilute the mud and thereby reduce the density. As indicated at about 4 hours the density returned to about 9.5 pounds per gallon. The gauge calibration was verified at about 4.1 hours by displacing the mud in the gauge conduit 12 with water. The reading was 8.34 pounds per gallon indicating accurate calibration. Upon resuming operations, the mud properties remained relatively constant.

Figure 6:
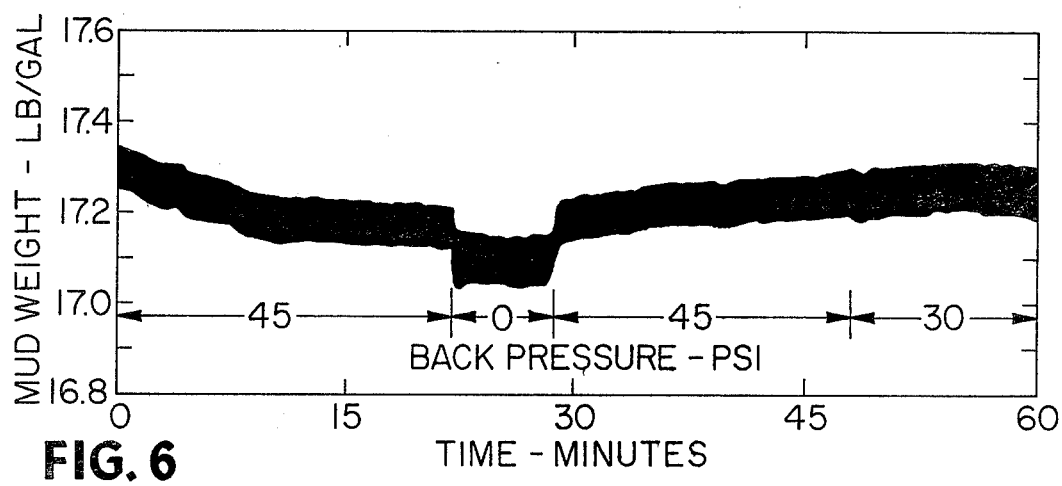

As mentioned previously, it has been found that in measuring the density of mud which is to be pumped into a well, the maintenance of a back pressure on the gauge conduit 12 is preferred to eliminate or substantially reduce the effects of gas (including air) entrained in the mud. The gas may be present in the mud as a result of mud agitation when adding weighting materials such as barite, operation of some equipment to remove drilled solids from the mud, or entrained in certain types of fluid loss additives. FIG. 6 illustrates the effect of gas in the mud. The same instrument described above was operated at 45 pounds per square inch (gauge pressure) back pressure for about 20 minutes during which the density leveled off to a value of about 17.1 pounds per gallon. The back pressure was then reduced to zero; the mud density immediately dropped to a value slightly above 17.0 pounds per gallon. Upon returning the back pressure to 45 and even 30 pounds per square inch, the effects of gas were substantially reduced.

Figure 8:
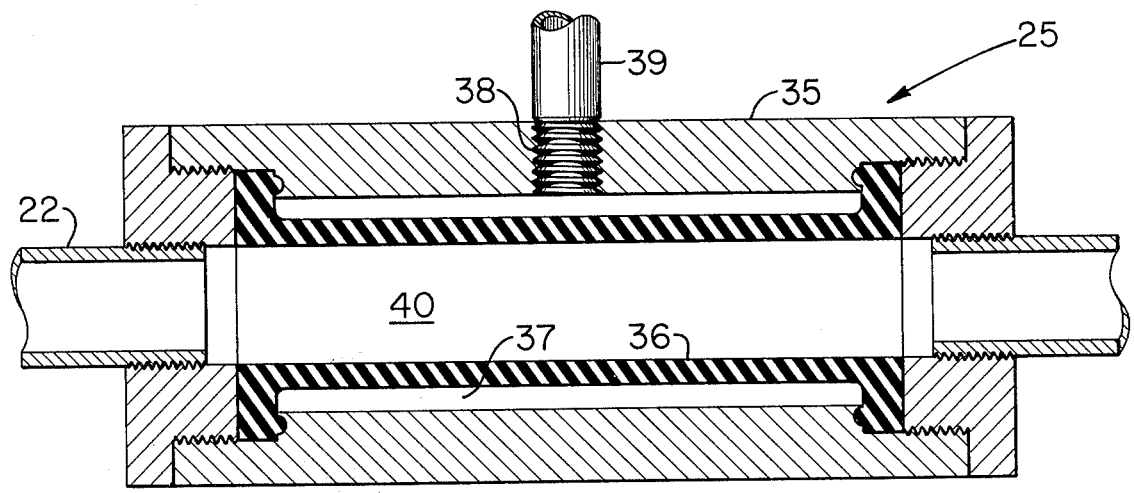
FIG. 8 is a longitudinal, sectional view of a suitable back pressure valve for the system disclosed in FIGS. 2, 3 and 4.

The back pressure valve 25 must be of construction that prevents plugging or caking by the mud. It is preferred that the back pressure valve be an elastomeric-sleeve pinch-type valve such as that illustrated in FIG. 8. The valve connects to discharge line 22 and generally includes a housing 35 which has mounted therein a rubber sleeve 36. The housing 35 and sleeve 36 define an internal annular chamber 37. A port 38 formed in the housing communicates with chamber and permits the pressurization of chamber 37 by line 39 which is connected to a suitable gas or fluid source. Passage 40 of sleeve 36 is straight and presents no obstructions. The pressure in chamber 37 determines the back pressure on the mud. The sleeve 36 pinches inwardly to throttle flow and thereby maintains the desired back pressure. The valve should be constructed of heavy duty material to enable long term, continuous trouble-free operation. A suitable air-operated, elastomeric sleeve ("pinch") valve for the practice of the present invention is the Type "DW" valve which is sold by Red Valve Company.

Figure 9:
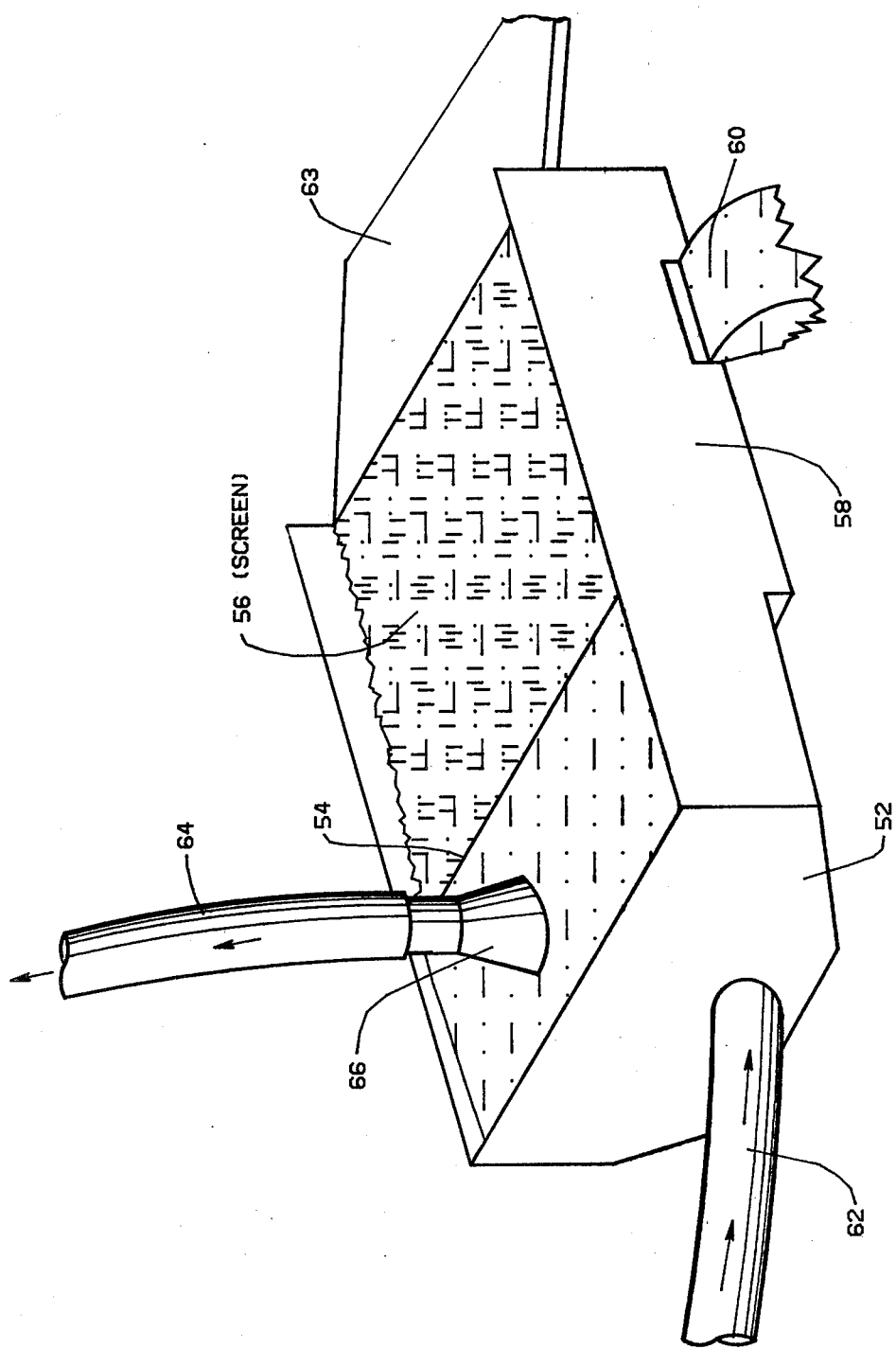
FIG. 9 is a perspective view of the one preferred embodiment of the inlet means of the present invention disposed in a shale shaker.

One of the purposes in monitoring the density of return mud exiting the well is to detect the presence of entrained formation gases in the mud. The density of the return mud is compared with the density of the input mud to detect the presence of formation gases. The density of the mud should be measured without back pressure. Further, in order to accurately determine the amount of entrained formation gases in the mud, it is desirable to measure the density of the mud before the mud is processed through any of the solids removal equipment, such as the shale shaker. Such processing will cause the mud to lose entrained formation gas, thereby resulting in an inaccurate determination of the amount of entrained gases in the mud. Referring to FIG. 9, there is shown a typical solids removal processing unit, called a shale shaker, used in drilling operation. The shale shaker comprises generally a flow distribution tank 52, weirs 54, one or more screens 56, collection tray 58 and discharge opening 60. A mud return line 62 is connected to the top of the blowout preventer and transports the return mud from the wellbore to the flow distribution tank 52. The flow distribution tank is provided with adjustable weirs 54 and is positioned adjacent to collection tray 58. The collection tank is provided with a shale shaker screen 56. The return mud flows from the top of the distribution tank over the adjustable weirs and onto the shale shaker screen. The shale shaker screen functions to remove drill cuttings from the mud. The cuttings are retained on the screen and are moved down the shale slide 63 to a reserve pit. The processed mud falls through the screen into the collection tray 54 and passes out the discharge opening 60. The screened mud is normally flowed into other tanks for further processing.

Figure 10:
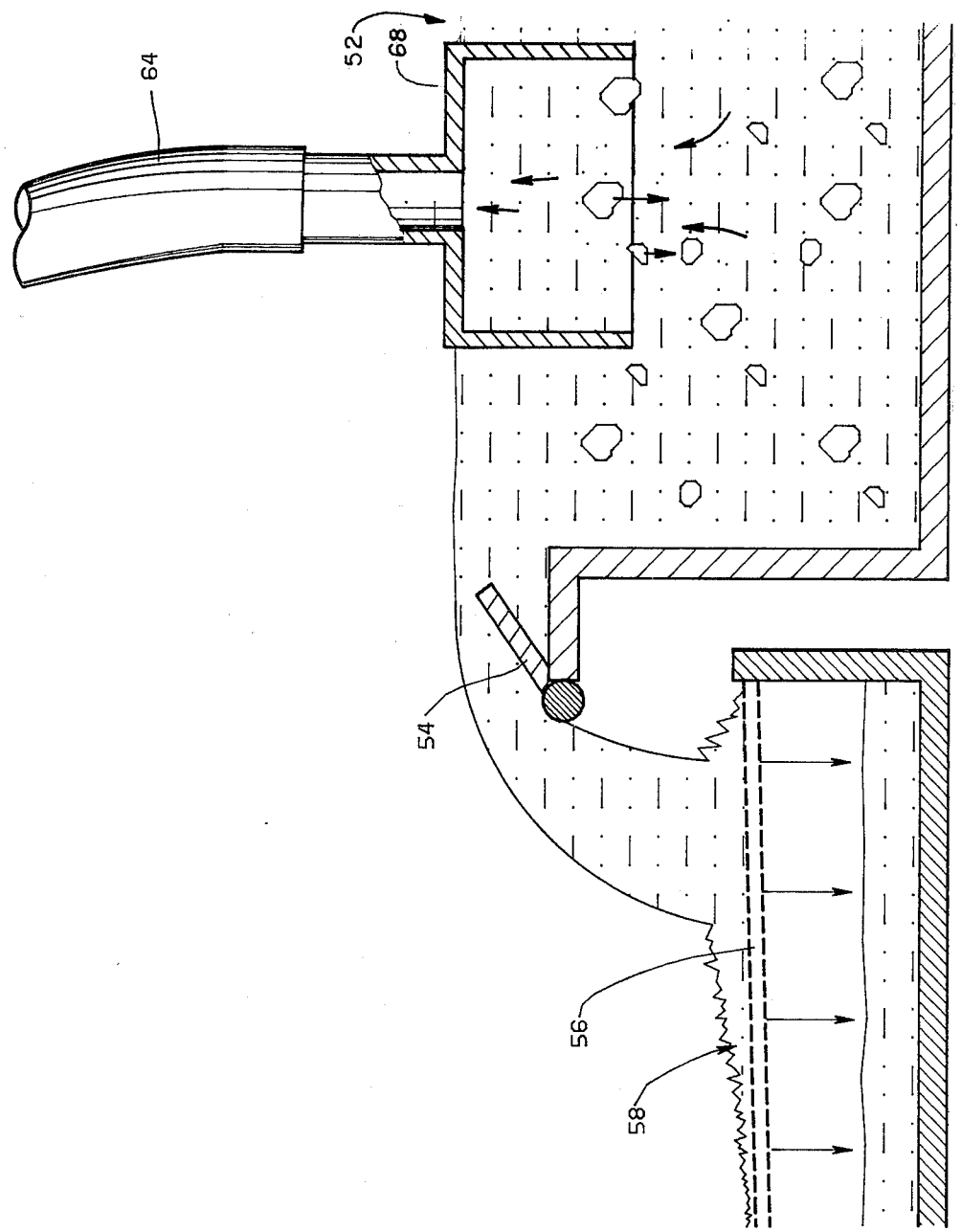
FIG. 10 is a cross sectional view of another preferred embodiment of the inlet means of the present invention disposed in a shale shaker.

In the present invention, the mud which is to be tested is preferably drawn off from the flow distribution tank 52 into the apparatus for measuring the fluid properties by a suction line 64. The mud is drawn from the flow stream prior to passing through the shale shaker to avoid the loss of the entrained formation gases. In the apparatus of the present invention, the largest vertical conduit is normally the gauge conduit. Therefore, the lowest fluid velocity in the apparatus will be in the gauge conduit and any settling of entrained solids will most likely occur in this portion of the apparatus. In order to prevent the larger drilling cuttings in the return mud from entering the suction line and settling out of the flow stream in the gauge conduit, the suction line is provided with means for preventing the larger drill cuttings from flowing into the suction line. Screens and the like are unsuitable because they readily become clogged with the drilling mud. The means of the present invention for preventing the larger drill cuttings from being drawn into the suction line generally comprises an outwardly flared inlet means 66 which is positioned in the mud stream in the flow distribution tank in a non-horizontal and preferably vertical attitude so that gravity opposes the flow of mud into the inlet means. The outwardly flared inlet means functions to reduce the upward velocity of the mud which is drawn into the inlet means. At the lower mud velocity, gravity causes most of the larger drill cuttings to fall out of the mud stream as the mud moves upward through the inlet and into the suction line. The inlet is sized so that the vertical component of the mud velocity in the area defined by the inlet is less than the lowest mud velocity in the apparatus. Thus any drill cuttings which are drawn into the suction line through the inlet means will pass through the apparatus without settling out of the mud stream. The outwardly flared inlet of the suction line effectively prevents most large drill cuttings from entering the apparatus; thereby avoiding the associated problems of plugging and the like. In FIG. 9, the inlet means is shown having a frusto-conical shape. However, it will be obvious to one skilled in the art that the inlet means may be formed in other shapes such as a cap shape as shown in FIG. 10. After the mud passes through the apparatus, it is returned to the flow distribution tank 52 through discharge line 67. The mud may also be returned to the top of the shale shaker screen 56.

Referring to FIG. 10, there is shown an alternative embodiment of the inlet means for removing large drill cuttings from the mud stream where like reference numerals indicate corresponding components. The inlet means comprises an inlet formed in the shape of a cap 68. The cap is sized so that the average vertical component of the mud velocity within the area defined by the cap is less than the lowest mud velocity in the apparatus. It is preferred that the cross-sectional flow area of the inlet means be from one-half to four times the cross-sectional flow area of the gauge conduit which is normally the largest vertical conduit. Most preferably, the cross sectional flow area of the inlet means will be equal to or greater than the cross sectional flow area of the gauge conduit. For example, if the diameter of the gauge conduit in the apparatus is 4 inches, the cap should also preferably have a diameter of 4 inches or more.

It will be obvious to one skilled in the art that the other flow conduits in the apparatus should be sized to have cross-sectional flow areas large enough to pass drill cuttings which are drawn into the suction line through the inlet means.

Figure 11:
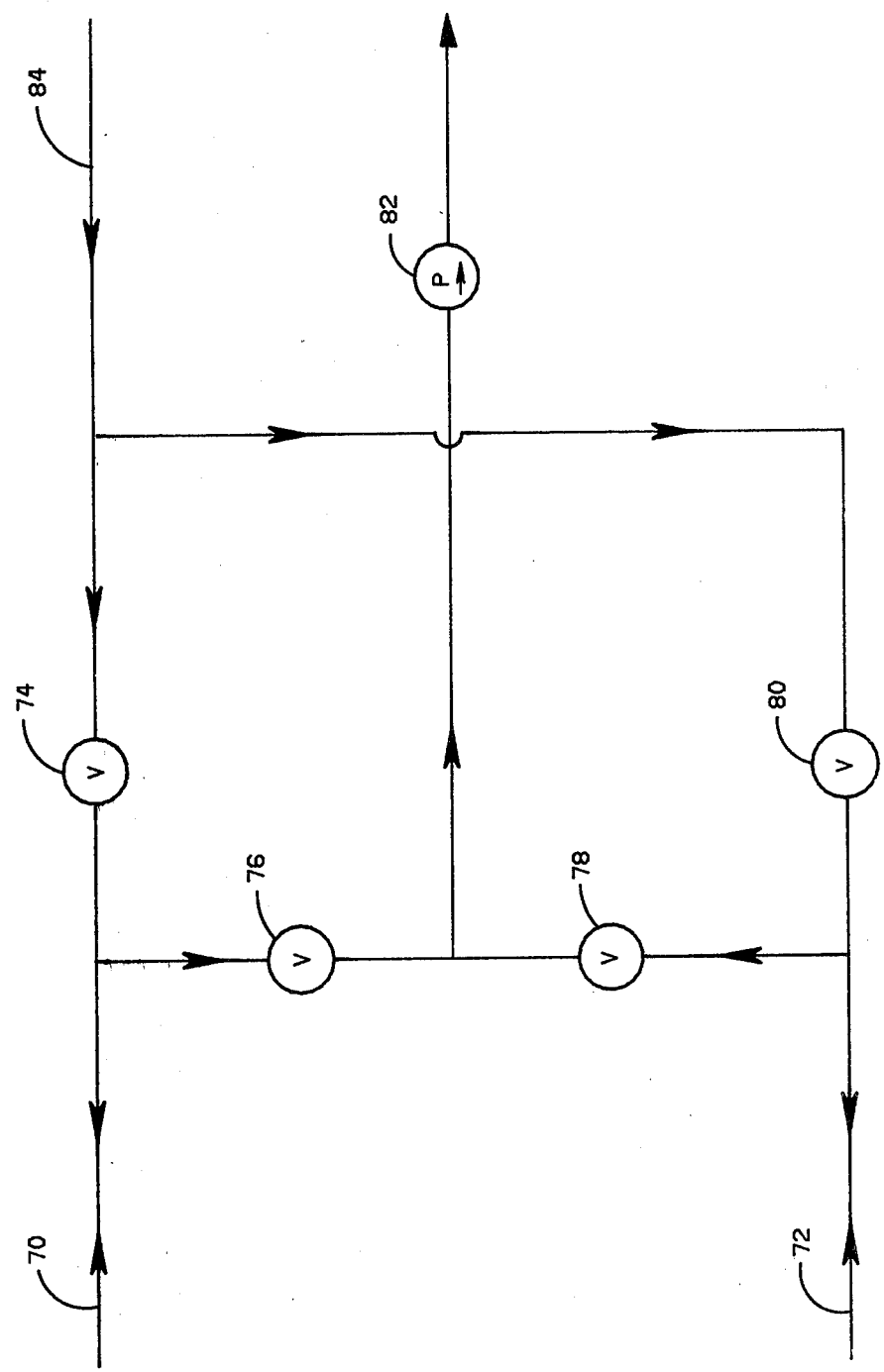
FIG. 11 is a schematic diagram of a piping and valve system for use in the present invention.

Referring to FIG. 11, there is shown a suitable piping and valve system which facilitates the prevention of large drill cuttings from flowing into the apparatus for measuring the fluid properties. In operation the direction of flow in the suction and discharge lines is periodically reversed to thereby backflush the lines and remove any drill cuttings which may have been drawn into the lines. When the flow is reversed, the suction line becomes the discharge line and the discharge line becomes the suction line. In this embodiment both the suction line and the discharge line are provided with the inlet means described above. In the first flow mode, line 70 is the suction line and line 72 is the discharge line. Valves 74 and 78 are closed and valves 76 and 80 are open. The mud is drawn off from the flow distribution tank by line 70. The intake mud passes through valve 76, pump 82 and flows into the apparatus. The mud is returned from the apparatus through line 84. The mud passes through valve 80 and flows through line 72 back into the flow distribution tank. In the second flow mode, valves 74 and 78 are open and valves 76 and 80 are closed. The mud is drawn off from the flow distribution tank by line 72. The mud passes through valve 78, pump 82 and flows into the apparatus. The mud is returned from the apparatus through line 84. The mud passes through valve 74 and flows through line 70 back into the flow distribution tank.

In a typical operation, the direction of the flow would be alternated every 30 to 60 seconds, depending upon the flow rate and the size of the flow lines. Suitable valves for the flow system are the elastomeric-sleeve, pinch-type valves such as the Mini-Flex Series 2600 valves manufactured by the Red Valve Co. The backflushing of the flow lines functions to remove any large drill cuttings which may have been drawn into the lines before they cause plugging of the pump or apparatus.

The principle of the invention and the best mode in which it is contemplated to apply that principle have been described. It is to be understood that the foregoing is illustrative only and that other means and techniques can be employed without departing from the true scope of the invention defined in the claims.

What is claimed is:

1. An apparatus for measuring the properties of a liquid which comprises:
   (a) a nonhorizontal conduit positioned to conduct liquid therethrough,
   (b) means for measuring the pressure differential between two vertically spaced locations in said conduit,
   (c) means for flowing liquid through said conduit at a rate where the shear rate of the flowing liquid is in the range of greater than zero to about 20 sec$^{-1}$,
   (d) means for cyclically interrupting flow of liquid through said conduit to provide a flow interval and a static interval, and
   (e) means for measuring the differential pressure between said spaced locations during the static interval.

2. Apparatus as defined in claim 1 and further comprising means for maintaining a sufficient back pressure on said conduit to reduce substantially the effects of gas entrained in said mud.

3. Apparatus as defined in claim 2 wherein said means for maintaining back pressure includes a valve connected to said conduit downstream of said differential pressure measuring means and including a housing and an elastomeric sleeve which in combination define a pressure chamber, and means for delivering a predetermined pressure to said chamber, said sleeve being inwardly deformable by pressure in said chamber to throttle flow therethrough to maintain said back pressure on said conduit.

4. Apparatus as defined in claim 1 and further comprising means for maintaining a pressure on liquid flowing through said conduit of at least two atmospheres.

5. Apparatus as defined in claim 1 wherein said conduit has an average flow area between said vertically spaced locations of not more than 52 square inches.

6. Apparatus as defined in claim 1 wherein said means for interrupting flow provides a cycling frequency of between about 0.1 cycle and about 15 cycles per minute.

7. Apparatus as defined in claim 1 wherein the means for flowing liquid through said conduit is operative to flow liquid upwardly through said conduit.

8. An apparatus for measuring fluid properties comprising:
   (a) a longitudinal conduit positioned in a nonhorizontal attitude,
   (b) a first flexible isolation diaphragm having an inner surface communicating with said conduit and an outer surface communicating with a chamber containing a noncompressible fluid,
   (c) a second isolation diaphragm having an inner surface communicating with said conduit and an outer surface communicating with a chamber containing a noncompressible fluid, (d) means operably associated with said conduit for moving a fluid upwardly through said conduit at a controlled rate where the shear rate of the flowing column of greater than zero to about 20 sec$^{-1}$, interrupting the flow of the fluid so that said fluid is alternately flowed through said conduit and held therein without flow, (e) differential pressure transducer means communicating with said outer chambers for measuring the pressure difference in said sample fluid in the conduit between said first and second isolation diaphragms, (f) means operably associated with said differential pressure transducer for indicating the pressure difference in said sample fluid in the conduit between said first and second isolation diaphragms, (g) means for cycling fluid flow through said conduit at a predetermined frequency, and (h) means for comparing the pressure difference in said sample fluid when said fluid is held in said conduit without flow indicating true density and when the fluid is flowing indicating an apparent density comprising the true density and a frictional pressure gradient density, said frictional pressure gradient density being proportional to the gel strength of said fluid.

9. The apparatus according to claim 8 wherein said differential pressure transducer is connected to each isolation diaphragm outer chamber by a conduit containing the same, noncompressible fluid as in said outer chamber and for this includes means for dampening the output of said transducer to filter out signal frequencies outside a predetermined range.

10. The apparatus according to claim 8 having a throttle valve for causing a back pressure in said conduit, located downstream from said isolation diaphragms.

11. The apparatus as defined in claim 8 wherein said means for cycling flow through said conduit includes means for reversing flow therethrough.

12. An apparatus for measuring the properties of liquid which comprises:
   (a) a conduit positioned in a nonhorizontal attitude and adapted to conduct liquid therethrough;
   (b) means for measuring pressure differential between two vertically spaced locations positioned along said conduit;
   (c) an inlet line connected to one end of said conduit;
   (d) a discharge line connected to the other end of said conduit;
   (e) a bypass line interconnecting said inlet line and said discharge line;
   (f) valve means for alternately directing flow through said conduit and said bypass line;
   (g) a back pressure valve connected to said discharge line downstream of said bypass line connection;
   (h) pump means connected to said inlet line upstream of said bypass line, said pump means being adapted to pump liquid continuously during measurement of said liquid, said pump means adapted to pump liquid through said conduit at a flow rate where the shear rate of the flowing liquid is in the range of greater than zero to about 20 sec$^{-1}$, and
   (i) means for comparing the pressure differential measured when the fluid is flowing through the bypass line indicating a true density and when said fluid is flowing through said conduit indicating an apparent density comprising the true density and a frictional pressure gradient density, said frictional pressure gradient density being proportional to the gel strength of said fluid.

13. A method for measuring the properties of a fluid, comprising:
   (a) measuring the pressure of a static column of said fluid at two vertically spaced points,
   (b) determining the difference in pressure between said points to thereby indicate the true density of said fluid,
   (c) measuring the pressure of a flowing column of said fluid at said two points said flowing column having a flow rate where the shear rate of the flowing fluid is in the range of greater than zero to about 20$^{-1}$,
   (d) determining the difference in pressure between said points during flow to thereby indicate an apparent density comprising the true density and a frictional pressure gradient density, said frictional pressure gradient density being proportional to the gel strength of said fluid.

14. The method according to claim 13 wherein said flow is upward and said apparent density is greater than said true density.

15. The method according to claim 13 wherein a pressure greater than atmospheric pressure is applied to said fluid during said measurements.

16. The method according to claim 15 wherein said pressure is up to about 10 atmospheres.

17. The method according to claim 13 wherein said measurements and determinations are cyclically repeated.

18. A method of measuring the properties of a fluid comprising the steps of:
   (a) flowing a fluid through a substantially vertical conduit,
   (b) terminating said flow to retain a static column of fluid in said conduit,
   (c) measuring the pressure of said static column of fluid at vertically spaced points in said conduit,
   (d) determining the difference in pressure between said points to indicate the true density of said fluid,
   (e) restarting said flow of fluid and flowing said fluid at a flow rate where the shear rate of the flowing fluid is in the range of greater than zero to about 20 sec$^{-1}$,
   (f) measuring the pressure of said flowing fluid at said points, and
   (g) determining the difference in pressure between said points during flow to indicate an apparent density comprising the true density and a frictional pressure gradient density, said frictional pressure gradient density being proportional to the gel strength of said fluid.

19. A method of monitoring the gel strength of a drilling fluid:
   (a) generating a first signal proportional to the difference in static pressure of a liquid in a conduit at two vertically spaced points to indicate the true density of the liquid,
   (b) thereafter, generating a second signal proportion to the difference in pressure between said points during flow of the liquid through the conduit at a flow rate where the shear rate of the flowing liquid is in a range of greater than zero to about 20 sec$^{-1}$ to thereby indicate an apparent density comprising the true density and a frictional pressure gradient density, and (c) comparing the first signal with the second signal to determine the difference therebetween, the difference being indicative of the gel strength of the drilling fluid.

20. An apparatus for measuring the density of a liquid which comprises:
   (a) a nonhorizontal conduit positioned to conduct liquid therethrough,
   (b) means for measuring the pressure differential between two vertically spaced locations in said conduit,
   (c) means for flowing liquid through said conduit,
   (d) means for cyclically interrupting flow of liquid through said conduit to provide a flow interval and a static interval,
   (e) means for measuring the differential pressure between said spaced locations during the static interval, and
   (f) means for maintaining a sufficient back pressure on said conduit to reduce substantially the effects of entrained gas in said liquid, said mean includes a valve connected to said conduit downstream of said differential pressure measuring means and including a housing and an elastomeric sleeve which in combination define a pressure chamber, and means for delivering a predetermined pressure to said chamber, said sleeve being inwardly deformable by pressure in said chamber to throttle flow therethrough to maintain said back pressure on said conduit.

21. The apparatus as defined in claim 20 wherein said back pressure means maintains a pressure on liquid flowing through said conduit of at least two atmospheres.

22. An apparatus for measuring the density of a liquid which comprises:
   (a) a nonhorizontal conduit positioned to conduct liquid therethrough,
   (b) an outwardly flared inlet means disposed on the end of said conduit, said inlet means positioned in a generally vertical attitude and sized so that the vertical component of the liquid velocity in the area defined by the inlet means is less than the minimum liquid velocity through said apparatus.
   (c) means for measuring the pressure differential between two vertically spaced locations in said conduit.
   (d) means for flowing liquid through said conduit,
   (e) means for cyclically interrupting flow of liquid through said conduit to provide a flow interval and a static interval, and
   (f) means for measuring the differential pressure between said spaced locations during the static interval.

* * * * *